United States Patent [19]

Burton, Jr. et al.

[11] Patent Number: 4,888,175

[45] Date of Patent: Dec. 19, 1989

[54] ASEPTIC PACKAGING

[76] Inventors: Kenneth R. Burton, Jr., 1327 Emerald Green Blvd., Houston, Tex. 77094; Charles B. Turner, 19418 Leafwood, Houston, Tex. 77084

[21] Appl. No.: 270,947

[22] Filed: Nov. 14, 1988

[51] Int. Cl.$^4$ ..................... A01N 43/38; A01N 43/56
[52] U.S. Cl. ................... 424/409; 424/411; 424/412; 424/404; 424/414
[58] Field of Search ............... 514/504; 424/83, 404, 424/412, 413, 414, 411, 415, 409

[56] References Cited

U.S. PATENT DOCUMENTS

| | | | |
|---|---|---|---|
| 3,069,252 | 12/1962 | Josephs et al. | 514/504 |
| 3,864,468 | 7/1975 | Hyman et al. | 424/413 |
| 4,663,077 | 5/1982 | Rei et al. | 514/504 |
| 4,666,706 | 5/1987 | Farquharson | 424/412 |

OTHER PUBLICATIONS

CA 89(25): 213852d, "Study of Aseptic Packaging of Foods by Using 2—(4—Thiazolyl) Benzimidazole in Plastic Film", 1978, Inoue, Mayumi.

Primary Examiner—Joseph L. Schofer
Assistant Examiner—Carmen Pili-Curtis
Attorney, Agent, or Firm—Neal J. Mosely

[57] ABSTRACT

An aseptic package of a material susceptible to bacterial or viral infection utilizes a film or sheet of a plastic packaging material having a biocidal agent dissolved or dispersed therein. The biocidal agent comprises 10,10-oxybisphenoxarsine or a biocidal derivative or analog thereof, in an amount sufficient to inhibit biocidal activity in the contents of the package. The biocidal agent is present in solution in or in combination with a plasticizer for the plastic sheet or film in an amount from 0.001 to 5.0% by weight of the plastic. The sheet or film is a hydrocarbon-based material, such as a polyalkylene resin or polyolefin, e.g., polyethylene or polypropylene. The biocidal agent is present in solution in or in combination with a plasticizer for the plastic sheet or film. The enclosed material may be an organic product, such as a food or a plant or may be formed in the shape of a dispensible liner for bath tubs. The utilization of the packaging sheet or film may also be considered as a novel method of inhibiting bacterial or viral growth in an organic material wherein the organic material is enclosed in a package of a film or sheet of a plastic packaging material having a biocidal agent dissolved or dispersed therein.

6 Claims, 1 Drawing Sheet

ASEPTIC PACKAGING

BACKGROUND OF THE INVENTION

1. Field of the Invention

This invention relates to new and useful improvements in packaging, and, more particularly, to packaging which inhibits bacterial activity in the material packaged and on the surface of the packaging material.

2. Brief Description of the Prior Art

The prior art discloses a number of examples of plastic film or sheet packaging materials which contain small amounts of biocidal materials for preventing bacterial attack on the film itself. This prior art, however, does not show the use of biocidal materials in packaging films or sheets at a level such that the contents of a package made therefrom are inhibited against bacterial or viral growth.

LIU et al U.S. Pat. No. 4,617,328 discloses that cellulosic, plastics, or film-forming polymer compsns. which are made up in continuous form are protected against attack by bacteria, fungi and antinomycetes by incorporating into the compsn. (or continuous form) or by coating with various known agricultural, microbicides, bactericides and paint preservatives. They can be fabricated into a continuous form against attack by bacteria, fungi or actinomycetes, are thermally stable at more than 148 deg. C. without deterioration, are able to migrate through compsn. to be dissipated throughout, and are stable towards ultraviolet and other light radiation. Compounds having formula: Y-(1,4-phenylene)-SO2-CH=CH—CN, in which Y is hydrogen, halogen, or C1-C4 alkyl; R1 AND R2 are independently hydrogen or methyl; and N is 1 or 2, are effective biocides or biostats for protection of plastic, polymeric or cellulosic materials against attack by microorganisms.

Gutman et al U.S. Pat. Nos. 4,388,249 and 4,331,480 disclose that compounds of the formula:

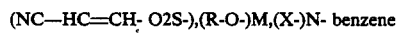

(NC—HC=CH- O2S-),(R-O-)M,(X-)N- benzene in which R is lower alkyl; X is halogen or lower alkyl; M is 1 OR 2; and N is 0, 1, 2 OR 3, are effective biocides or biostats for protection of plastic or polymeric materials against attack by microorganisms.

Rei U.S. Pat. Nos. 4,661,528 and 4,663,359 disclose a composition comprising a dry blend mixture of a porous thermoplastic resin powder and from 1 to 80 wt. % of a microbiocide based upon the weight of the mixture. The microbiocide is present in the mixture at a concentration of at least about 20 times greater than the normal upper usage concentration of the microbiocide, and is held within the pores of the thermoplastic powder. The resulting concentrate is a substantially non-dusting, free-flowing powder which is readily incorporated into a second thermoplastic resin to product a resulting article having the appropriate level of microbiocide. The resin is polyvinyl chloride, polyethylene, polystyrene, polypropylene, nylon, styrenebutadiene copolymer, polycarbonate, polystyrene-polyphenylene oxide blend, polyphenylene oxide or an ethylene/acrylic acid salt ionomer. The microbiocide is 10,10'-oxybisphenoxarsine; N(trichloromethylthio)-4-cyclohexene-1,2-dicarboxinide; 2,3,5 trichloro-4-propylsulfo 2,3,4,5-tetrachloro-4(methylsulfonyl)pyridine; zinc salt of 1-hydroxypyridine-2thione; N-(trichloromethylthio)phthalimide; N-(2methylnaphthyl)meleimide; cis-N-(1,1,2,2-tetrachloroethyl-thio4-cyclohexene-1,2-dicarboximide; 1-isopropyl-3-methyl pyrazolyl-5-dimethyl carbamate; 3-,ethyl pyrazoyl dimethylcarbamate; manganese ethylene bisdithiocarbamate; zinc ethylene bisdithiocarbamate; disodium ethylene bisdithiocarbamate; ferric dimethyl dithiocarbamate; zinc dimethyl dithiocarbamate; 2,4-dinitro-6-capryl phenol crotonate; p-chlorophenyl-p-chlorobenzene sulfonate; 2-N-octyl-4-isothiazol in-3-one; methyl(butyl carbamoyl)-2-benzimidazole carbamate; 2-(4thiazole) benzimidazole; copper 8-hydroxylquinolinate; alpha-diethoxyphosphinodithioacetylurea; alpha dimethoxylphosphinodithioacetylurea; diethoxyphosphinodithioacetamide dimethoxyphosphinodithioacetamide; bis(dimethylamido)phosphoryl fluoride; 2-cyclohexyl-3-isothiazolone; 4,5-dichloro-2cyclohexyl-3-isothiazolone or tributyl tin fluoride.

Hill et al U.S. Pat. No. 4,086,297 discloses that a solid composition comprising a homogeneous mixture of a solid thermoplastic resin and from 1 to 80 weight % of a microbiocide which is insoluble in water is readily dispersible or soluble in the resin at temperatures sufficiently high to permit plastic manipulation of the resin and the dispersion or solution of the microbiocide is sustained indefinitely upon cooling to ambient temperature while the diffusivity of the microbiocide in the resin under such conditions becomes vanishingly small, retains its microbiocidal activity in the resin and does not degrade or react with the resin in which it is dispersed. This composition provides a convenient non-toxic dosage from of the microbiocide which is subsequently mixed with a second thermoplastic resin at a concentration of about 0.5 to 15 weight % to obtain a homogeneous resin composition containing an effective amount of the microbiocide.

Pupp U.S. Pat. No. 4,461,667 discloses a packing material for aseptic packages having the interior coated with polyethylene and extruded to give a separable, bacteria tight package.

Knopick et al U.S. Pat. No. 4,164,941 discloses a disposable drape for a surgical overhead table where the drape is liquid-proof and covers the entire surface of the associated table. Also, the drape is of a construction which will prevent the passage of any bacteria through the surface area of the drape.

Several publications are also pertinent to the use of biocidal agents in plastic materials for protection of the material against degredation:

Inoue, Mayumi (Ventron Biocide Res. Inst., Japan) in JOURNAL: Bokin Bobai (1978) VOL. 6 NO. 6, pp. 250–7 reviews vinyzene antimicrobial plastics.

FLEXIBLE STERILE CLOSURE SYSTEM FOR CONTAINERS INHIBITING BIOSLIMES ON SURFACES OF POLYETHYLENE TUBING, Ford, H. W.; Altermatt, W. E.; Hamilton, N. F. Univ of Florida, Lake Alfred, FL, USA Drainage Design and Management, Proceedings of the Fifth National Drainage Symposium Chicago, IL, Dec 14–15, 1987 Sponsored by: ASAE, St. Joseph, MI, U.S.A.; American Soc of Agronomy, Madison, WI, USA; ASCE, New York, N.Y., U.S.A.; Corrugated Plastic Tubing Assoc; Corp Science Soc of America, Madison, WI, U.S.A.; et al E.I. Conference No.: 11232 Source: ASAE Publication 07-87. Publ. by ASAE, St. Joseph, MI, USA p 416–423 (1987): A new approach for the control of microbial-induced clogging of plastic drain pipes involves incorporating an antimicrobial compounds into the resin at the time of manufacture of the drain tubing. Any compound added to polyethylene for drain pipe applications to inhibit bioslimes must be compatible with the resin system and have stable properties when in contact with soil and water. Slow release of the antimicrobial compound would provide the required long-term performance. The treated pipe must be safe for surface water and control ochre when applied at EPA-approved treatment levels. In the studies described in this paper, Vinyzene (REGISTERED) SB-1 PR, was used as the biocide in polyethylene materials. Bio-Flow is the name for SB-1 PR incorporated in a specially designed orange-colored pipe containing 4. 7 and 12. 5 cm holes. Laboratory tests, simulated drain experiments, and the results of 30 months of field testing are described.

Kirk-Othmer Encyclopedia, chapter on Industrial Antimicrobial Agents: Arsenicals. 10,10′-Oxybisphenoxyarsine is the only organoarsenic product of importance as an industrial antimicrobial agent. The active ingredient is a colorless microcrystalline powder, but it is sold only in dilute formulations to minimize toxicity. Vinyzene solutions are used primarily for the plastic industry; Vinyzene is sold at 1% or 2% concentration in various plasticizers, eg, epoxidized soybean oil and various phthalate esters (qv), and at 5% as a pelletized solid polymeric resin (81). A 1% solution in 1,4-butanediol is provided for use in polyurethanes (88). The Durotex solution that is used in the textile industry is 2% active and is formulated with nonionic, cationic, or anionic emulsifiers (82). Although many arsenic compounds are generally recognized as being toxic, the 10,10-oxybisphenoxyarsine products are claimed to be less toxic because the arsenic is organically bound. Nonetheless, when undiluted, the active ingredient is a skin and eye irritant; however, the products are diluted in order to minimize toxicity (see Arsenic compounds).

SUMMARY OF THE INVENTION

One of the objects of this invention is to provide a new and improved aseptic package of a material susceptible to bacterial or viral infection.

Another object of this invention is to provide a new and improved aseptic package of a material susceptible to bacterial or viral infaction in which the material is enclosed in a film or sheet of a plastic packaging material having a biocidal agent dissolved or dispersed therein.

Another object of this invention is to provide a new and improved aseptic package of a material susceptible to bacterial or viral infaction in which the material is enclosed in a film or sheet of a plastic packaging material having a biocidal agent dissolved or dispersed therein which comprises 10,10-oxybisphenoxarsine or a biocidal derivative or analog thereof, in an amount sufficient to inhibit biocidal activity in the contents of said package.

Another object of this invention is to provide a new and improved aseptic package of a material susceptible to bacterial or viral infaction in which the material is enclosed in a film or sheet of a plastic packaging material having a biocidal agent dissolved or dispersed therein in solution in or in combination with a plasticizer for said plastic sheet or film.

Still another object of this invention is to provide a new and improved aseptic package of a material susceptible to bacterial or viral infaction in which the material is enclosed in a film or sheet of a plastic packaging material having a biocidal agent dissolved or dispersed therein in solution in or in combination with a plasticizer for said plastic sheet or film in an amount from 0.001 to 5.0% by weight of the plastic.

Still another object of this invention is to provide a new and improved aseptic package of a material susceptible to bacterial or viral infaction in which the material is enclosed in a film or sheet of a hydrocarbon-based plastic packaging material having a biocidal agent dissolved or dispersed therein in solution in or in combination with a plasticizer for said plastic sheet or film in an amount from 0.001 to 5.0% by weight of the plastic.

Still another object of this invention is to provide a new and improved aseptic package of a material susceptible to bacterial or viral infaction in which the material is enclosed in a film or sheet of a polyalkylene plastic packaging material having a biocidal agent dissolved or dispersed therein in solution in or in combination with a plasticizer for said plastic sheet or film in an amount from 0.001 to 5.0% by weight of the plastic.

Yet another object of this invention is to provide a new and improved aseptic package of a material susceptible to bacterial or viral infaction in which the material is enclosed in a film or sheet of a polyolefin packaging material having a biocidal agent dissolved or dispersed therein in solution in or in combination with a plasticizer for said plastic sheet or film in an amount from 0.001 to 5.0% by weight of the plastic.

Yet another object of this invention is to provide a new and improved aseptic package of a material susceptible to bacterial or viral infaction in which the material is enclosed in a film or sheet of a polyethylene or polypropylene plastic packaging material having a biocidal agent dissolved or dispersed therein in solution in or in combination with a plasticizer for said plastic sheet or film in an amount from 0.001 to 5.0% by weight of the plastic.

Another object of this invention is to provide a new and improved aseptic package of an organic product susceptible to bacterial or viral infaction in which the material is enclosed in a film or sheet of a plastic packaging material having a biocidal agent dissolved or dispersed therein.

Another object of this invention is to provide a new and improved aseptic package of a plant or seeds of a plant susceptible to bacterial or viral infaction in which the material is enclosed in a film or sheet of a plastic packaging material having a biocidal agent dissolved or dispersed therein.

Another object of this invention is to provide a new and improved packaging material comprising a sheet or film of a polyolefin containing 0.001-%5.0% by weight of a biocidal agent comprising 10,10-oxybisphenoxarsine or a biocidal derivative or analog thereof, in an amount sufficient to inhibit biocidal activity in the contents of a package made from the material.

Still another object of this invention is to provide a new and improved packaging material comprising a sheet or film of a polyolefin containing 0.001-%5.0% by weight of a biocidal agent comprising 10,10-oxybisphenoxarsine or a biocidal derivative or analog thereof, in an amount sufficient to inhibit biocidal activity and formed in the shape of a dispensible liner for bath tubs.

Still another object of this invention is to provide a new and improved method of inhibiting bacterial or viral growth in an organic material which comprises enclosing said organic material in a package of a film or sheet of a plastic packaging material having a biocidal agent dissolved or dispersed therein.

Yet another object of this invention is to provide a new and improved method of inhibiting bacterial or viral growth in an organic material which comprises enclosing said organic material in a package of a film or sheet of a plastic packaging material having a biocidal agent dissolved or dispersed therein, the biocidal agent comprising 10,10-oxybisphenoxarsine or a biocidal derivative or analog thereof, in an amount sufficient to inhibit biocidal activity in the contents of said package.

Yet another object of this invention is to provide a new and improved method of inhibiting bacterial or viral growth in an organic material which comprises enclosing said organic material in a package of a film or sheet of a plastic packaging material having a biocidal agent dissolved or dispersed therein, the biocidal agent comprising 10,10-oxybisphenoxarsine or a biocidal derivative or analog thereof, in an amount sufficient to inhibit biocidal activity in the contents of said package in the range from about 0.001 to 5.0% by weight of the plastic.

Other objects of this invention will become apparent from time to time throughout the specification and claims as hereinafter related.

The foregoing objects and other objects of this invention are accomplished by an aseptic package of a material susceptible to bacterial or viral infection utilizes a film or sheet of a plastic packaging material having a biocidal agent dissolved or dispersed therein. The biocidal agent comprises 10,10-oxybisphenoxarsine or a biocidal derivative or analog thereof, in an amount sufficient to inhibit biocidal activity in the contents of the package. The biocidal agent is present in solution in or in combination with a plasticizer for the plastic sheet or film in an amount from 0.001 to 5.0% by weight of the plastic. The sheet or film is a hydrocarbon-based material, such as a polyalkylene resin or polyolefin, e.g., polyethylene or polypropylene. The biocidal agent is present in solution in or in combination with a plasticizer for the plastic sheet or film. The enclosed material may be an organic product, such as a food or a plant or may be formed in the shape of a dispensible liner for bath tubs. The utilization of the packaging sheet or film may also be considered as a novel method of inhibiting bacterial or viral growth in an organic material wherein the organic material is enclosed in a package of a film or sheet of a plastic packaging material having a biocidal agent dissolved or dispersed therein.

DESCRIPTION OF THE PREFERRED EMBODIMENTS

Antibiocidal plastic films (0.1 mil–10 mil) and sheets (20 mil and thicker) are prepared by incorporating therein the biocide 10,10'-Oxybisphenoxarsine, or an analog or homolog thereof, at a level of 0.001–5.0% wt. of the film or sheet.

10,10'-Oxybisphenoxarsine is the only organoarsenic product of importance as an industrial antimicrobial agent. The active ingredient is a colorless microcrystalline powder, but it is sold only in dilute formulations to minimize toxicity. It is sold under the trademark Vinyzene in solution and in pellet form.

Vinyzene solutions are used primarily for the plastic industry; Vinyzene is sold at 1% or 2% concentration in various plasticizers, eg, epoxidized soybean oil and various phthalate esters, and at 5% in pellets of solid polymeric resin. A 1% solution in 1,4-butanediol is provided for use in polyurethanes. A solution used in the textile industry is 2% active and is formulated with nonionic, cationic, or anionic emulsifiers.

Although many arsenic compounds are generally recognized as being toxic, the 10,10-oxybisphenoxarsine products are claimed to be less toxic because the arsenic is organically bound. Nonetheless, when undiluted, the active ingredient is a skin and eye irritant; however, the products are diluted in order to minimize toxicity. Vinyzene has received EPA certification (Reg. No. 2828-115) for use as a biocide.

Figure 1:
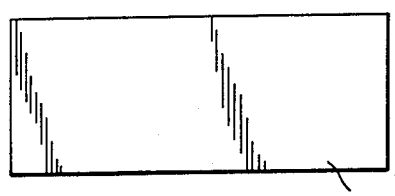
FIG. 1 is a plan view of a sheet of plastic film or sheet material prepared in accordance with is invention.
Figure 2:
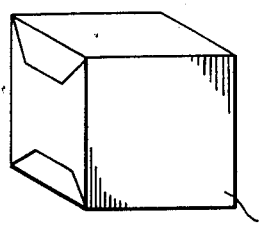
FIG. 2 is an isometric view of a package made from a material in accordance with this invention.
Figure 3:
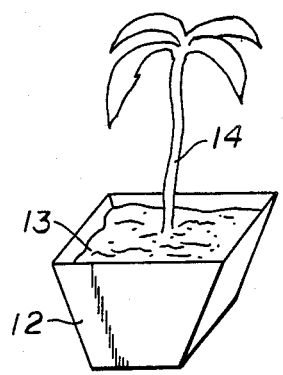
FIG. 3 is an isometric view of a plant having its root structure supported in a package made from a material in accordance with this invention.

Referring to the drawings by numerals of reference, in FIG. 1, there is shown a plan view of a plastic film (0.1 mil–10 mil) or sheet (20 mil and thicker) are prepared by incorporating therein the biocide 10,10'-Oxybisphenoxarsine, or an analog or homolog thereof, at a level of 0.001–5.0% wt. of the film or sheet 10. In FIG. 2, the sheet or film 10 is shown formed into a package 11 containing an organic material susceptible to bacterial or viral attack. The material in the package may be a food product or or living plants or any other material requiring protection. In FIG. 3, there is shown a package 12 containing the soil and root structure 13 of a plant 14. In each of these figures, the material which is packaged is itself protected against bacterial or viral attack as distinguished from merely protecting the packaging sheet or film against attack. Packages made from the sheet or film 10 may be completely enclosed as in FIG. 2 or open as in FIG. 3. Packages may also be in the form of preformed tubes which may be subsequently closed.

EXAMPLE 1

A series of tests were carried out to determine the effects on Vinyzene impregnated plastic film 10 (used in the packages shown in FIGS. 2 and 3) on the growth and development of the bacterium *Xanthomonas campestris* (the causal agent of black rot on cabbage). Four circular disks of untreated polyethylene film and four disks of polyethylene containing 0.006% 10,10-oxybisphenoxyarsine (Vinyzene) were placed on individual inoculated Petri dishes containing Potato Dextrose Agar (PDA). The inoculum consisted of nonquantified, turbid bacterial suspension pipetted evenly and spread on the surface of the PDA plates (1 ml. per plate).

The circular disks were cut with a #5 stainless steel cork borer and surface-sterilized with a 20% Chlorox (sodium hypochlorite) solution for 15 seconds, rinsed in sterile distilled water and then placed on plates under sterile conditions. Four disks were applied per plate. Four plates were used for each treatment giving a total of sixteen replicates per treatment.

Plates were taken from the incubator (27° C.) 24 hours after inoculation and zones of inhibition were measured:

TABLE I

| Plate No. | Disk | Zones of Inhibition (mm.) | |
|---|---|---|---|
| | | Vinyzene Treated | Untreated |
| A | 1 | 3.5 | 0.0 |
| A | 2 | 2.0 | 0.0 |
| A | 3 | 4.5 | 0.0 |
| A | 4 | 4.5 | 0.0 |
| B | 1 | 4.5 | 0.0 |
| B | 2 | 4.5 | 0.0 |
| B | 3 | 4.5 | 0.0 |
| B | 4 | 7.0 | 0.0 |
| C | 1 | 2.0 | 0.0 |
| C | 2 | 4.5 | 0.0 |
| C | 3 | 5.5 | 0.0 |
| C | 4 | 5.5 | 0.0 |
| D | 1 | 5.5 | 0.0 |
| D | 2 | 3.5 | 0.0 |
| D | 3 | 4.5 | 0.0 |
| D | 4 | 3.0 | 0.0 |

It was concluded that the Vinyzene-impregnated film showed consistent bacteriostatic properties on the plant pathogenic bacterium used as a test organism.

EXAMPLE 2

A series of tests were carried out to determine the effects on Vinyzene impregnated plastic film on the growth and development of the fungus *Fusarium solani* (a common soil borne fungus). Four circular disks of untreated polyethylene film and four disks of polyethylene containing 0.006% 10,10-oxybisphenoxyarsine (Vinyzene) were placed on individual inoculated Petri dishes containing Potato Dextrose Agar (PDA). The inoculum consisted of non-quantified, turbid spore solution that was dispersed over the surface of each plate. Inoculation was done prior to application of the circular disks.

The circular disks were cut with a #5 stainless steel cork borer and surface-sterilized with a 20% Chlorox (sodium hypochlorite) solution for 15 seconds, rinsed in sterile distilled water and then placed on plates under sterile conditions. Four disks were applied per plate. Four plates were used for each treatment giving a total of sixteen replicates per treatment.

Plates were taken from the incubator (27° C.) 24 hours after inoculation and zones of inhibition were measured:

TABLE II

| Plate No. | Disk | Zones of Inhibition (mm.) | |
|---|---|---|---|
| | | Vinyzene Treated | Untreated |
| A | 1 | 7.0 | 0.0 |
| A | 2 | 7.0 | 0.0 |
| A | 3 | 7.0 | 0.0 |
| A | 4 | 6.0 | 0.0 |
| B | 1 | 9.0 | 0.0 |
| B | 2 | 7.0 | 0.0 |
| B | 3 | 8.0 | 0.0 |
| B | 4 | 8.0 | 0.0 |
| C | 1 | 8.0 | 0.0 |
| C | 2 | 7.0 | 0.0 |
| C | 3 | 7.0 | 0.0 |
| C | 4 | 7.0 | 0.0 |
| D | 1 | 8.0 | 0.0 |
| D | 2 | 8.0 | 0.0 |
| D | 3 | 8.0 | 0.0 |
| D | 4 | 7.0 | 0.0 |

It was concluded that the Vinyzene-impregnated film showed consistent bacteriostatic properties on the plant pathogenic fungus used as a test organism.

ANOTHER EMBODIMENT

Figure 4:
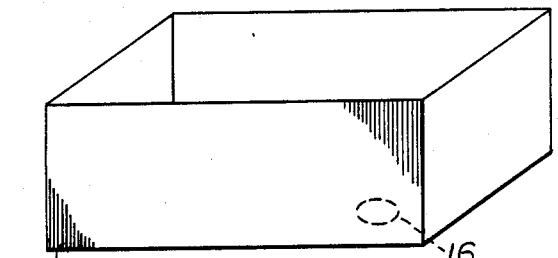
FIG. 4 is an isometric view of a sanitary bathtub liner produced according to this invention.

In FIG. 4, the sheet or film 10 of Vinyzene impregnated polyethylene film 10 is formed into a rectangular, boxshaped liner 15 for use in sanitary applications, such as a sanitary replaceable liner for hospital bath tubs. Liner 15 is shaped to fit the bath tube (not shown) and has openings for any tub fittings and a bottom opening 16 positioned to fit the drain opening in the tub.

EXAMPLE 3

Two samples of bath tub liner material 15 were evaluated for resistance to bacteria and fungi. One film was 5 mil. Vinyl impregnated with 0.006% 10,10-oxybisphenoxyarsine (Vinyzene) in the plasticizer for the Vinyl film. The other film was an untreated 5 mil. Vinyl control. The treated films were resistant to bacteria and fungi while the untreated films were not.

The first test procedure was for bacterial resistance. The samples were placed on nutrient agar inoculated with (1) *Staphylococus aureus*, ATCC 6538 and (2) *Klebsiella pneumoniae*, ATCC 4352. After 24 hours incubation at 37° C., antibacterial activity was evaluated by measuring (in mm.) the size of a clear zone of no growth (Zone of Inhibition) around each sample, and visually determining growth in the contact ares.

Bacterial growth is rated by the following scale:
No Growth Contact Area (NGCA)

This is a designation frequently used in bacterial tests. Bacterial organisms are difficult to determine on the sample itself, so the area immediately under the sample is examined for growth. This is usually a passing designation and indicates that there were no bacterial colonies under the sample.
Growth Contact Area (GCA)

This indicates failure of the sample since colonies of bacteria are detected immediately under the sample in contact with the same.

The test results are in Table 3 below:

TABLE 3

| | Qualitative Bacterial Resistance | |
|---|---|---|
| Sample | Zone of Inhibition (mm) *Staphylococus aureus* | Growth in the Contact Area *Klebsiella pneumoniae* |
| Vinyzene treated | 12/NGCA | 6/NGCA |
| Control | 0/GCA | 0/GCA |

The next test procedure was the New York State Proposal #1241 (Sept. 5, 1985). The samples were quantitatively evaluated for bacteriostatic activity by placing 0.2 ml. of diluted culture of the test bacteria ($10^5$ organisms) in direct contact with the sterilized sample. After 24 hours incubations at 37° C. and 100% R.H., the sample was diluted with sterile letheen broth and the number of surviving organisms determined by the standard count. The percent survival was calculated by comparison to an untreated control film. Maximum N.Y. State Spec. Requirements are (1) *Staphylococus aureus* 2% survival and (2) *Klebsiella pneumoniae*, 17% survival.

TABLE 4

Quantitative Bacterial Resistance
After 24 Hours Incubation at 37° C.

| Sample | Staphylococus aureus | | Klebsiella pneumoniae | |
| --- | --- | --- | --- | --- |
| | # Surviving Bacteria | % Survival | # Surviving Bacteria | % Survival |
| Vinyzene treated | ≬100 | 0.02 | $9.1 \times 10^2$ | 0.23 |
| Control | $2.0 \times 10^8$ | ≬100 | $6.1 \times 10^8$ | ≬100 |

The final test procedure was for mildew resistance. The samples were placed on (non-nutrient) mineral salts agar and inoculated with a mixed fungal spore suspension of *Aspergillus niger* ATCC 9642; *Penicillium funiculosum* ATCC 9644; *Chaetomium globusum* ATCC 6205; *Aureobasidium pullulans* ATCC 9348; and *Gliocladium virens* ATCC 9645. After 21 days incubation at 28° C., antifungal activity was evaluated by visually rating the degree of fungal growth on the samples.

Surface fungal growth is rated by the following scale:

| | |
| --- | --- |
| No growth | (NG) |
| Traces of growth (less than 10% coverage) | (TG) |
| Light Growth (10–30% coverage) | (LG) |
| Moderate Growth (30–60% coverage) | (MG) |
| Heavy Growth (60% to complete coverage) | (HG) |
| ASTM Rating | |
| 0 = No growth | |
| 1 = Traces of growth | |
| 2 = Light Growth | |
| 3 = Moderate Growth | |
| 4 = Heavy Growth | |

TABLE 5

| Sample | Mildew Resistance ASTM G-21-80/Surface Fungal Growth |
| --- | --- |
| Vinyzene treated | No Growth |
| Control | Light Growth |

While this invention has been described fully and completely, with emphasis on a few preferred embodiments, it should be understood that, within the scope of the appended claims, this invention may be practiced otherwise than as specifically described herein.

We claim:

1. An aseptic package of a plant with soil and root structure susceptible to bacterial or viral infection,
    said plant having its soil and root structure enclosed in a sheet of a plastic packaging material formed into an open top container having a biocidal agent dissolved or dispersed in said sheet in solution in or in combination with a plasticizer for said plastic sheet, in an amount from 0.001 to 5.0% by weight of said plastic,
    said biocidal agent comprising 10,10-oxybisphenoxarsine or a biocidal derivative or analog thereof, in an amount sufficient to inhibit biocidal activity on and throughout soil and root structure over an extended period of storage.

2. A package according to claim 1 in which said sheet is a hydrocarbon-based material.

3. A package according to claim 1 in which said sheet is a polyalkylene resin.

4. A package according to claim 1 in which said sheet is a polyolefin.

5. A package according to claim 1 in which said sheet is polyethylene.

6. A package according to claim 1 in which said sheet is polypropylene.

* * * * *